(12) United States Patent
Maa et al.

(10) Patent No.: US 11,369,711 B2
(45) Date of Patent: Jun. 28, 2022

(54) ULTRAVIOLET-FREE ANTIVIRAL AIR-FILTERING LIGHTING DEVICE

(71) Applicant: Aleddra Inc., Renton, WA (US)

(72) Inventors: Chia-Yiu Maa, Bellevue, WA (US); Chun-Te Yu, Bellevue, WA (US)

(73) Assignee: Aleddra Inc., Renton, WA (US)

( * ) Notice: Subject to any disclaimer, the term of this patent is extended or adjusted under 35 U.S.C. 154(b) by 0 days.

(21) Appl. No.: 17/182,534

(22) Filed: Feb. 23, 2021

(65) Prior Publication Data

US 2021/0299315 A1 Sep. 30, 2021

Related U.S. Application Data

(63) Continuation-in-part of application No. 17/147,783, filed on Jan. 13, 2021, which is a continuation-in-part of application No. 16/836,570, filed on Mar. 31, 2020, now Pat. No. 10,921,004.

(51) Int. Cl.
*A61L 9/18* (2006.01)
*H05B 45/20* (2020.01)
*F21K 9/237* (2016.01)
*F21Y 115/10* (2016.01)

(52) U.S. Cl.
CPC ............ *A61L 9/18* (2013.01); *A61L 2209/12* (2013.01); *A61L 2209/14* (2013.01); *F21K 9/237* (2016.08); *F21Y 2115/10* (2016.08); *H05B 45/20* (2020.01)

(58) Field of Classification Search
CPC .......... A61L 2209/12; A61L 9/20; A61L 9/18; A61L 9/205; A61L 2209/14; F21V 33/0044; F21V 29/00; F21V 33/0096; F21V 33/0088; F21V 23/003; F21V 33/0064; F21W 2131/30; E04B 9/02; F04D 25/08; F24F 2003/1667; F24F 3/1603; F24F 2003/1628; F24F 2003/1664; F21Y 2113/10; F21Y 2115/10; H05B 45/20;

(Continued)

(56) References Cited

U.S. PATENT DOCUMENTS

| 10,921,004 | B1 * | 2/2021 | Maa | ............................ F24F 8/10 |
| 2006/0280660 | A1 * | 12/2006 | Weiss | ........................ B01D 53/88 |
| | | | | 422/186.3 |
| 2020/0282097 | A1 * | 9/2020 | Baldi | ........................ B01J 21/063 |

* cited by examiner

*Primary Examiner* — Joseph L Williams
*Assistant Examiner* — Jose M Diaz
(74) *Attorney, Agent, or Firm* — Han IP PLLC; Andy M. Han (57) ABSTRACT

A lighting device that comprises a housing, a first visible light source, a second visible light source, an air filter, an airway, and an air circulation mechanism for each airway. The first visible light source contributes to the light output of the device, whereas the second visible light source is responsible for germicidal irradiation by activating a visible-light activatable photocatalytic coating on the air filter. The airway has an air inlet and an air outlet. The air circulation mechanism sucks an ambient air through the air inlet, forces the air through the air filter, and releases the air through the air outlet. The air filter traps airborne particles. The second visible light source is disposed adjacent to the air filter and activates a photocatalyst material in the antiviral photocatalytic coating. Airborne microbials trapped by the air filter are decomposed by the activated photocatalyst material in the antiviral photocatalytic coating.

22 Claims, 10 Drawing Sheets

(58) Field of Classification Search
CPC ........ H05B 47/165; F21S 8/026; F21K 9/232; F21K 9/237
See application file for complete search history.

ULTRAVIOLET-FREE ANTIVIRAL AIR-FILTERING LIGHTING DEVICE

CROSS-REFERENCE TO RELATED PATENT APPLICATION(S)

The present disclosure is part of a Continuation-in-Part (CIP) of U.S. patent application Ser. No. 17/147,783, filed 13 Jan. 2021, which is a CIP of U.S. patent application Ser. No. 16/836,570, filed 31 Mar. 2020 and issued as U.S. Pat. No. 10,921,004 on 16 Feb. 2021, the contents of which being incorporated by reference in their entirety.

BACKGROUND

Description of Related Art

In U.S. patent application Ser. No. 17/147,783, an antiviral air-filtering lighting device was introduced. The device includes a housing, a first light source, a second light source, an airway, an air filter, and an air circulation mechanism corresponding to the airway. The housing houses the first light source, the second light source, the airway, and the air filter. The first light source emits predominantly visible light (>400 nm) and accounts for at least 95% of the light output of the lighting device. The second light source is disposed inside the airway and contribute less than 5% of the light output of the lighting device, and emits predominantly an ultraviolet (UV) light (<400 mn). The airway has an air inlet and an air outlet. The air circulation mechanism sucks an ambient air through the air inlet, forces the air through the air filter, and releases the air through the air outlet. The air filter traps airborne particles. The UV dosage emitted out of the lighting device does not exceed a UV threshold limit value (TLV) dosage defined by American Conference of Governmental Industrial Hygienists (ACGIH). In some embodiments, the air filter has an antiviral photocatalytic coating on the surface. The second light source is positioned adjacent to the air filter and activates a photocatalyst material in the antiviral photocatalytic coating. The airborne microbials trapped by the air filter are decomposed by the activated photocatalyst material in the antiviral photocatalytic coating.

In U.S. Pat. No. 9,522,384, Liu L. et al. teaches the use of rhombus-shape anatase-type titanium dioxide ($TiO_2$) such that this new type of $TiO_2$ can be activated by visible light wavelengths and become germicidal active. In U.S. Pat. No. 10,874,762, Maa C. et al teaches the use of a light source and an air-permeable lampshade coated with a photocatalytic coating that can be activated by a visible light emitted by the light source. Considering these two teachings, it thus becomes feasible to modify the teaching in U.S. patent application Ser. No. 17/147,783 by using a visible light source for the second light source and a visible-light activatable photocatalytic coating on the air filter to deliver the same antiviral air-filtering functionality without using any ultraviolet (UV) light source. There are two benefits of using a visible light source for the second light source. Firstly, UV is a potential health hazard since it causes skin and eye damages to an occupant. If a UV-based second light source is not properly concealed in the airway, it may leak the UV wavelength into the environment. Or if a custodian tries to replace the air filter without turning off the UV-based second light source, the custodian could be exposed to UVC. By getting rid of the use of any UV light source, the new design is thus inherently safer. Secondly, UV light source tends to have a shorter life span, between 2000-5000 hours. This implies a replacement of the UV light source is due every 2000-5000 hours. When using a visible light source, such as white light LED, its life span easily exceeds 50,000 hours. This helps cutting down the maintenance cost significantly when using the antiviral air-filtering lighting device of the present disclosure.

SUMMARY

In one aspect, the lighting device comprises a housing, a first light source, a second light source, an air filter, an airway, and an air circulation mechanism corresponding to the airway. The housing houses the first light source, the second light source, the air filter, and the airway. The first light source emits predominantly a first visible light (>400 nm) and accounts for at least 90% of the light output of the lighting device. The second light source emits a second visible light with a wavelength greater than 400 nm and accounts for less than 10% of a light output of the lighting device. The second light source is disposed inside the airway. The airway has an air inlet and an air outlet. The air circulation mechanism sucks an ambient air through the air inlet, forces the air through the air filter, and releases the air through the air outlet. The air filter traps airborne particles carried in the air. The air filter has an antiviral photocatalytic coating activatable by any visible light (e.g., the first visible light and/or the second visible light) on a surface thereof. The second light source is disposed adjacent to the air filter and activates a photocatalyst material in the antiviral photocatalytic coating. Airborne microbials trapped by the air filter are decomposed by the activated photocatalyst material in the antiviral photocatalytic coating. In some embodiments, the second light source emits no ultraviolet (UV) wavelength (less than 400 nm), i.e., the second light source is UV-free.

The first light source provides general lighting, whereas the second light source, the air filter, the airway, and the air circulation mechanism together form an air-disinfection module. For most applications, the first light source and the air-disinfection module may be turned on and off at the same time, but this is not required. Sometimes, a user may choose to only turn on the first light source, e.g., when a teach wants to shut off the air-disinfection module off during a lecture for keeping the classroom quiet. Some other times, a user may choose to do the opposite, i.e., turning on only the air-disinfection module, e.g., in the situation where other regular lighting fixtures already provide sufficient light level for the space, thus no need for turning on the first light source. Therefore, it is foreseeable that the first light source and the air-disinfection module may be turned on and off independently.

In some embodiments, the visible-light activatable photocatalyst material in the antiviral photocatalytic coating contains one type of material, titanium oxide ($TiO_2$). It is also common to use $TiO_2$ with another metal for the metal may help $TiO_2$ absorb the energy in the visible light range. Therefore, in some embodiments, the photocatalyst material in the antiviral photocatalytic coating contains titanium oxide ($TiO_2$) as the primary photocatalyst and an active metal ingredient such as silver, gold, copper, zinc, nickel, or a combination thereof, as the secondary photocatalyst. Liu's teaching in U.S. Pat. No. 9,522,384 demonstrates the use of $TiO_2$ as the primary photocatalyst and silver as the secondary photocatalyst.

The titanium dioxide is classified as a semiconducting photocatalyst. Recently, technology breakthrough has demonstrated that noble metal nanoparticles such as gold (Au)

and silver (Ag) can are a class of efficient photocatalysts working by mechanisms distinct from those of semiconducting photocatalysts (https://pubs.rsc.org/en/content/article-landing/2013/gc/c3gc40450a#!divAbstract). The present disclosure is not limited to the use of semiconducting photocatalysts such as $TiO_2$ only. The metal-based photocatalysts would work just as well. Therefore, in some embodiments, the photocatalyst material in the antiviral photocatalytic coating contains a noble metal nanoparticle such as gold (Au) or sliver (Ag) as the main photocatalyst.

The visible wavelength may not have as strong photon energy as UV wavelength. When using a visible light to activate a visible-light activatable photocatalyst material, it would be helpful to use other means to improvement the photocatalytic efficiency. One option is to increase the size of the surface area of the air filter coated with the photocatalyst material. Therefore, in some embodiments, the air filter comprises multiple layers or folds, which effectively increase the size of the surface area of the air filter coated with the photocatalyst material. In some other embodiments, the air filter is of cylindrical shape, which again help enlarging the surface area of the air filter coated with the photocatalyst material.

In some embodiments, the air filter contains non-woven fabric, a material that is highly effective in capture airborne particles.

It is known that activated carbon can absorb and remove gases and bad odors. In some embodiments, the air filter contains activated carbon.

In some embodiments, the air circulation mechanism comprises at least one fan disposed in the airway. Another option to improve the air-filtering efficiency is the increase the air processing capability by using multiple fans. In some embodiments, the air circulation mechanism comprises a first fan and a second fan wherein the first fan sucks the ambient air into the airway and the second fan pulls the air out of the airway. This dual-fan configuration with a push (by the first fan) and a pull (by the second fan) of the air into and out of the airway, improves the air processing capability of the present disclosure, thus resulting a higher air-filtering efficiency.

In some embodiments, the first light source comprises light emitting diodes (LEDs) each emitting the first visible light. In some embodiments, the second light source comprises LEDs each emitting the second visible light. It is foreseeable to use a higher color temperature for the second light source because a higher color temperature tends to result in a higher light output, thus contributing to a higher photocatalytic efficiency, as compared to a light source with a lower color temperature.

In some embodiments, the first light source may further comprise a third light source and a fourth light source. Both emit predominantly visible lights (>400 nm), and the color temperature of the third light source is higher than the color temperature of the fourth light source. The use of the third light source with a higher color temperature is for providing a higher circadian stimulus, which is desirable for some lighting applications for mimicking the daylight. Similarly, the use of the fourth light source with a lower color is to provide a lower circadian stimulus for nighttime. Moreover, in some embodiments, the color temperature of the first light source may be tunable via a controller by mixing the combination ratio of color temperatures of the third light source and the fourth light source. This color tuning may be done manually, or it may be done automatically according to a circadian schedule stored in a memory module. The circadian schedule will transition the color temperature of the first light source from warm white (2700K) to cold white (6500K) at dawn and revert the color temperature back to warm white at sunset, thus emulating color transition of the sunlight.

As mentioned above, it is foreseeable that the first light source and the air-disinfection module may be turned on and off independently. Nonetheless, for an environment with an adequate light level provided by existing lighting fixtures, it would not be reasonable to use the present disclosure stated above without the intention of ever turning on the first light source. It would be much better of having a device with only the air-disinfection module, plus the housing, yet without the first light source. Therefore, in another aspect, the lighting device comprises a housing, a light source, an air filter, an airway, and an air circulation mechanism corresponding to the airway. The housing houses the light source, the air filter, and the airway. The light source emits a visible light with a wavelength greater than 400 nm. The light source is disposed inside the airway. The airway has an air inlet and an air outlet. The air circulation mechanism sucks an ambient air through the air inlet, forces the air through the air filter, and releases the air through the air outlet. The air filter traps airborne particles carried in the air. The air filter has an antiviral photocatalytic coating activatable by a visible light on a surface thereof. The light source is disposed adjacent to the air filter and activates a photocatalyst material in the antiviral photocatalytic coating. Airborne microbials trapped by the air filter are decomposed by the activated photocatalyst material in the antiviral photocatalytic coating. It is foreseeable the light emitted by the light source may be concealed inside the airway. It is also foreseeable to use a translucent housing where a portion of the light emitted by the light source may come out of the translucent housing.

In some embodiments, the light source emits no ultraviolet (UV) wavelength (less than 400 nm), i.e., the light source is UV-free.

In some embodiments, the visible-light activatable photocatalyst material in the antiviral photocatalytic coating contains one type of material, titanium oxide ($TiO_2$). Moreover, in some embodiments, the photocatalyst material in the antiviral photocatalytic coating contains titanium oxide ($TiO_2$) as the primary photocatalyst and an active metal ingredient such as silver, gold, copper, zinc, nickel, or a combination thereof, as the secondary photocatalyst.

In some embodiments, the air filter contains non-woven fabric, a material that is highly effective in capture airborne particles.

In some embodiments, the air circulation mechanism comprises at least one fan disposed in the airway.

In some embodiments, the light source comprises light emitting diodes (LEDs).

BRIEF DESCRIPTION OF THE DRAWINGS

The accompanying drawings are included to aid further understanding of the present disclosure, and are incorporated in and constitute a part of the present disclosure. The drawings illustrate a select number of embodiments of the present disclosure and, together with the detailed description below, serve to explain the principles of the present disclosure. It is appreciable that the drawings are not necessarily to scale, as some components may be shown to be out of proportion to size in actual implementation in order to clearly illustrate the concept of the present disclosure.

DETAILED DESCRIPTION OF PREFERRED EMBODIMENTS

Overview

Various implementations of the present disclosure and related inventive concepts are described below. It should be acknowledged, however, that the present disclosure is not limited to any particular manner of implementation, and that the various embodiments discussed explicitly herein are primarily for purposes of illustration. For example, the various concepts discussed herein may be suitably implemented in a variety of lighting devices having different form factors.

The present disclosure discloses a lighting device that comprises a housing, a first visible light source, a second visible light source, an air filter, an airway, and an air circulation mechanism for each airway. The first visible light source contributes to the light output of the device, whereas the second visible light source is responsible for germicidal irradiation by activating a visible-light activatable photocatalytic coating on the air filter. The airway has an air inlet and an air outlet. The air circulation mechanism sucks an ambient air through the air inlet, forces the air through the air filter, and releases the air through the air outlet. The air filter traps airborne particles. The second visible light source is disposed adjacent to the air filter and activates a photocatalyst material in the antiviral photocatalytic coating. Airborne microbials trapped by the air filter are decomposed by the activated photocatalyst material in the antiviral photocatalytic coating.

Example Implementations

Figure 1A:
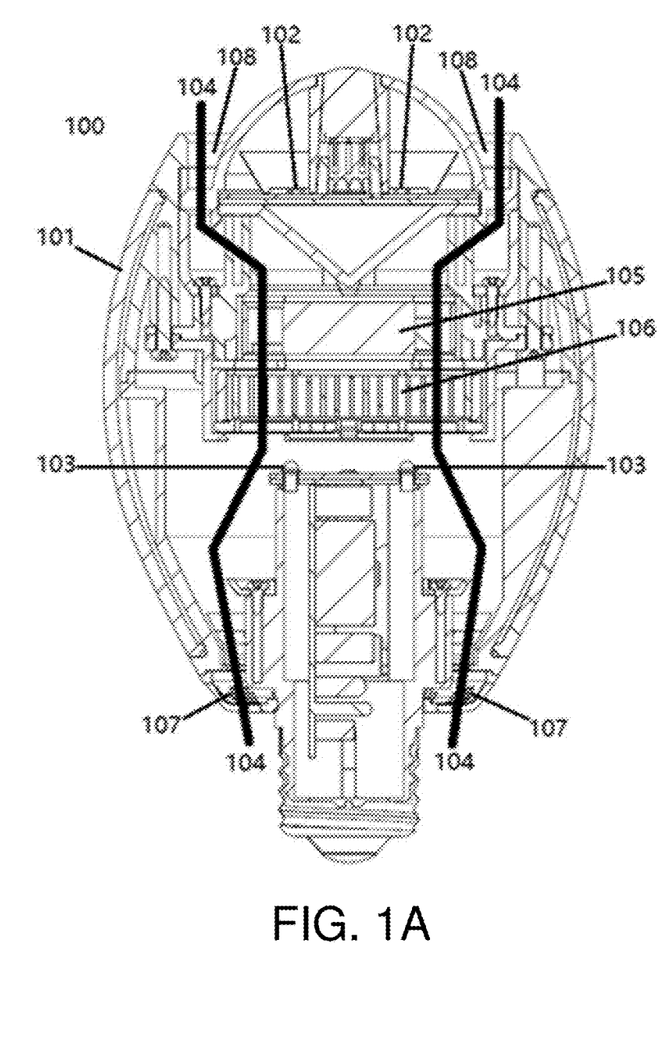
FIG. 1a schematically depicts a cross-section diagram of an LED screw-in lamp as an embodiment of the present disclosure.
Figure 1B:
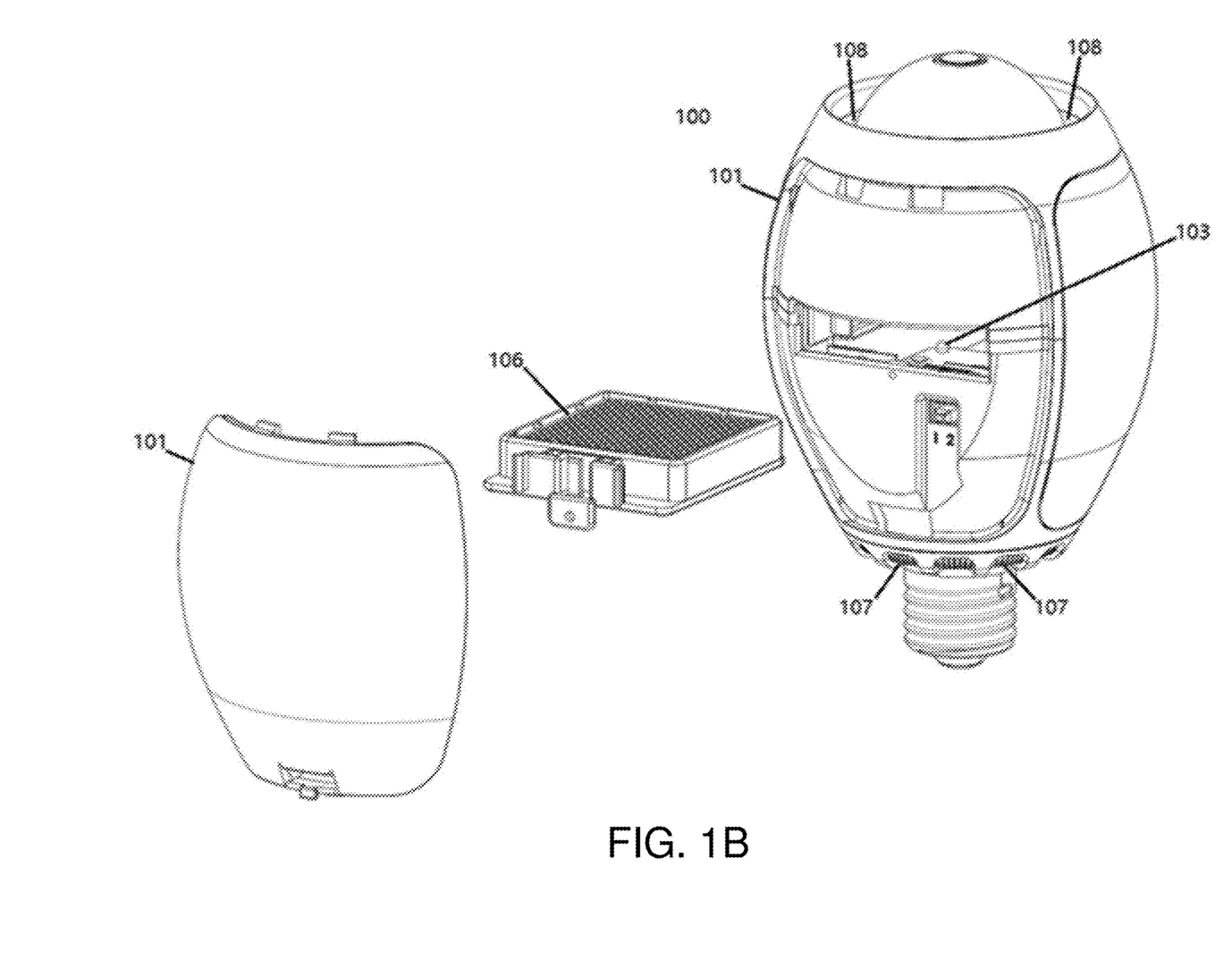
FIG. 1b schematically depicts a diagram of the screw-in lamp from another perspective.
Figure 1C:
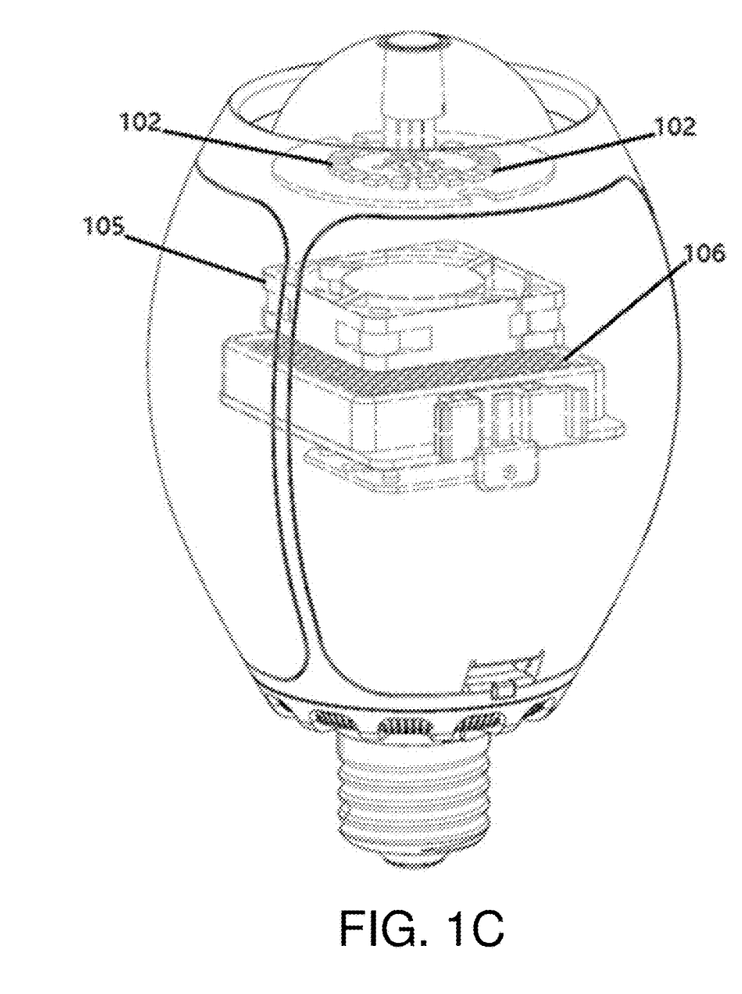
FIG. 1c schematically depicts a diagram of the screw-in lamp from yet another perspective.

FIG. 1a-1c show an embodiment of the lighting device of the present disclosure in a form of an LED screw-in lamp 100. This lamp has a housing 101, the first light source 102, the second light source 103, one airway 104, and one fan 105 and one air filter 106. The first light source 102 comprises multiple LEDs on top of the lamp emitting predominantly white light in the >400 nm wavelength range, and accounts for 100% light output of the lighting device. The second light source 103 comprises multiple LEDs emitting predominantly white light in the >400 nm wavelength range, and they are concealed inside the housing and have no contribution to the light output of the lighting device. The airway 104 has an air inlet 107 and an air outlet 108. The fan 105 and the air filter 106 are disposed inside the airway 104. The fan 105 sucks the ambient air through the air inlet 107, forces the air through the air filter 106, and releases the air through the air outlet 108. The air filter 106 has antiviral photocatalytic coating 109 on its surface. The second light source 103 is disposed adjacent to the air filter 106 for activating the photocatalyst material in the antiviral photocatalytic coating 109. In this embodiment, the second light source 103 is inside the airway 104.

Figure 1D:
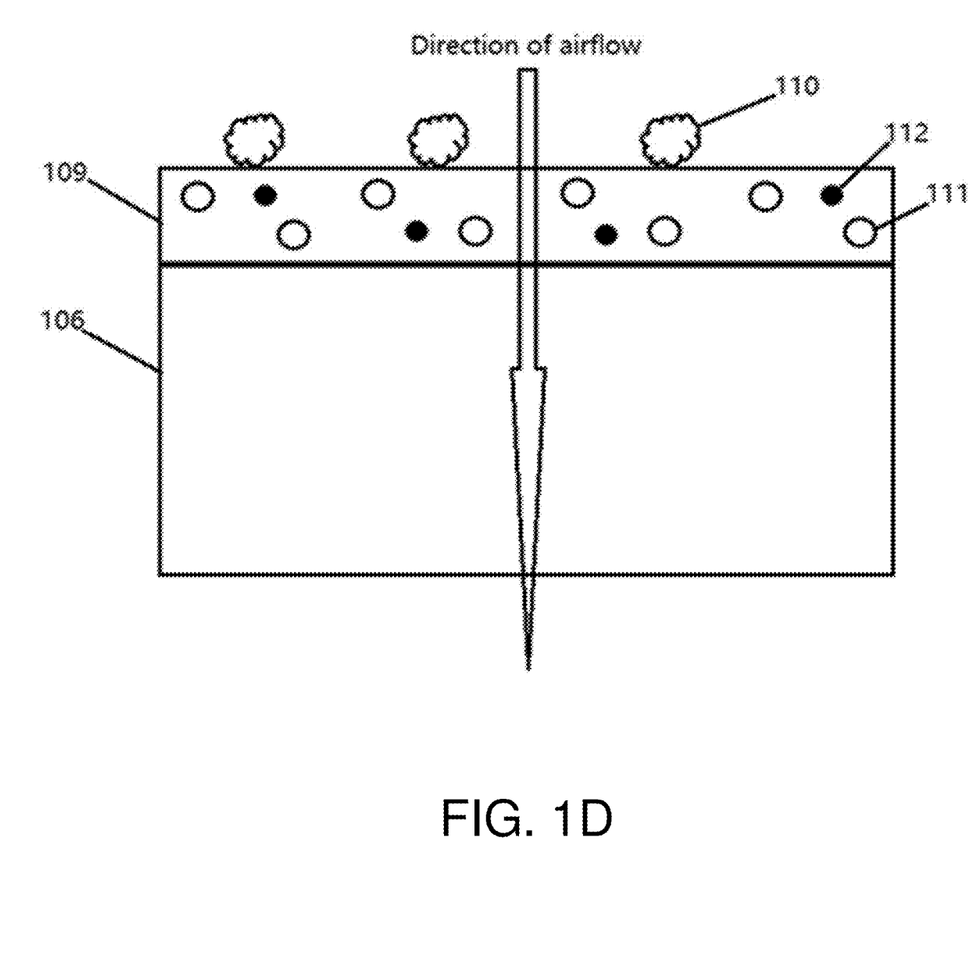
FIG. 1d schematically depicts the air filter and its antiviral photocatalytic coating of the lamp, and the trapped microbials.

In FIG. 1d, as the air passes through the air filter 106, the airborne microbials 110 are trapped on the surface of the air filter. The photocatalyst material in the antiviral photocatalytic coating 109 activated by the second light source 103 kills and decomposes the trapped microbials 110. The photocatalyst material contains nano anatase-type $TiO_2$ 111 as its primary photocatalyst and nano silver 112 as its secondary photocatalyst. It is foreseeable to use metals other than nano silver as the secondary photocatalyst. Moreover, it is anticipated to use noble metal nanoparticle such as gold (Au) and silver (Ag) as the main photocatalyst in lieu of a semiconducting photocatalyst $TiO_2$.

Figure 2A:
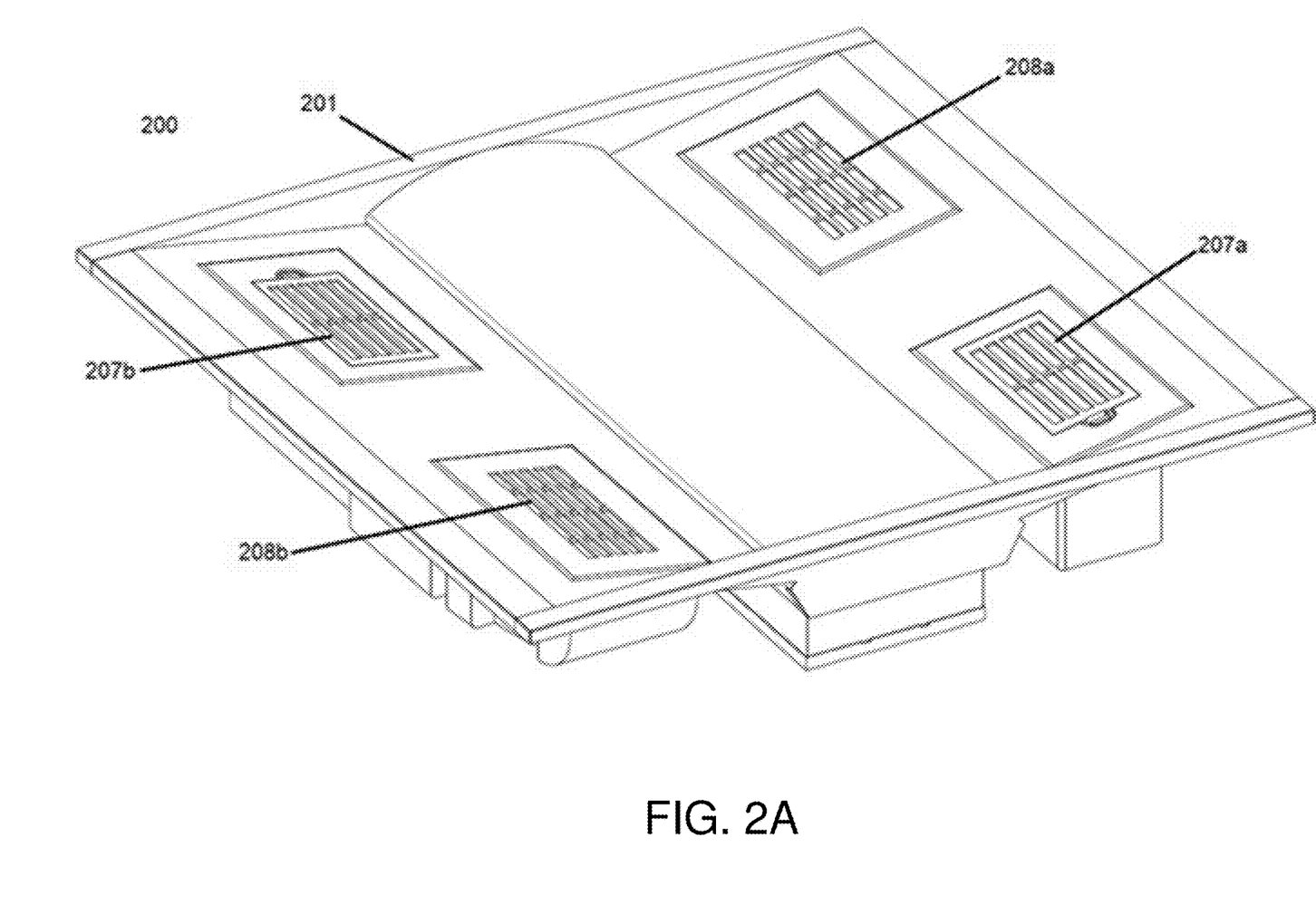
FIG. 2a schematically depicts an exterior view of an LED troffer fixture.
Figure 2B:
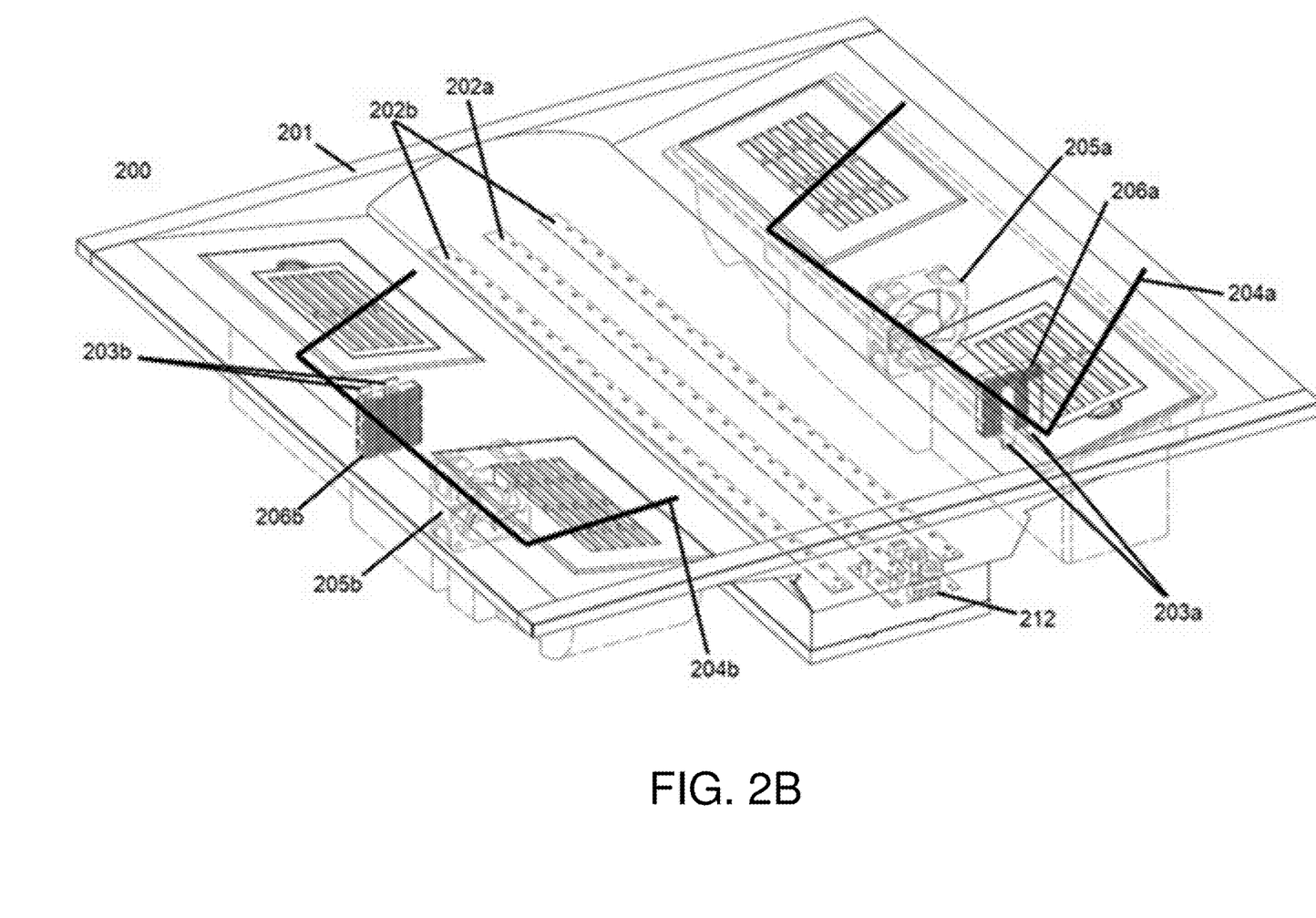
FIG. 2b schematically depicts a look-through view of the troffer.
Figure 2C:
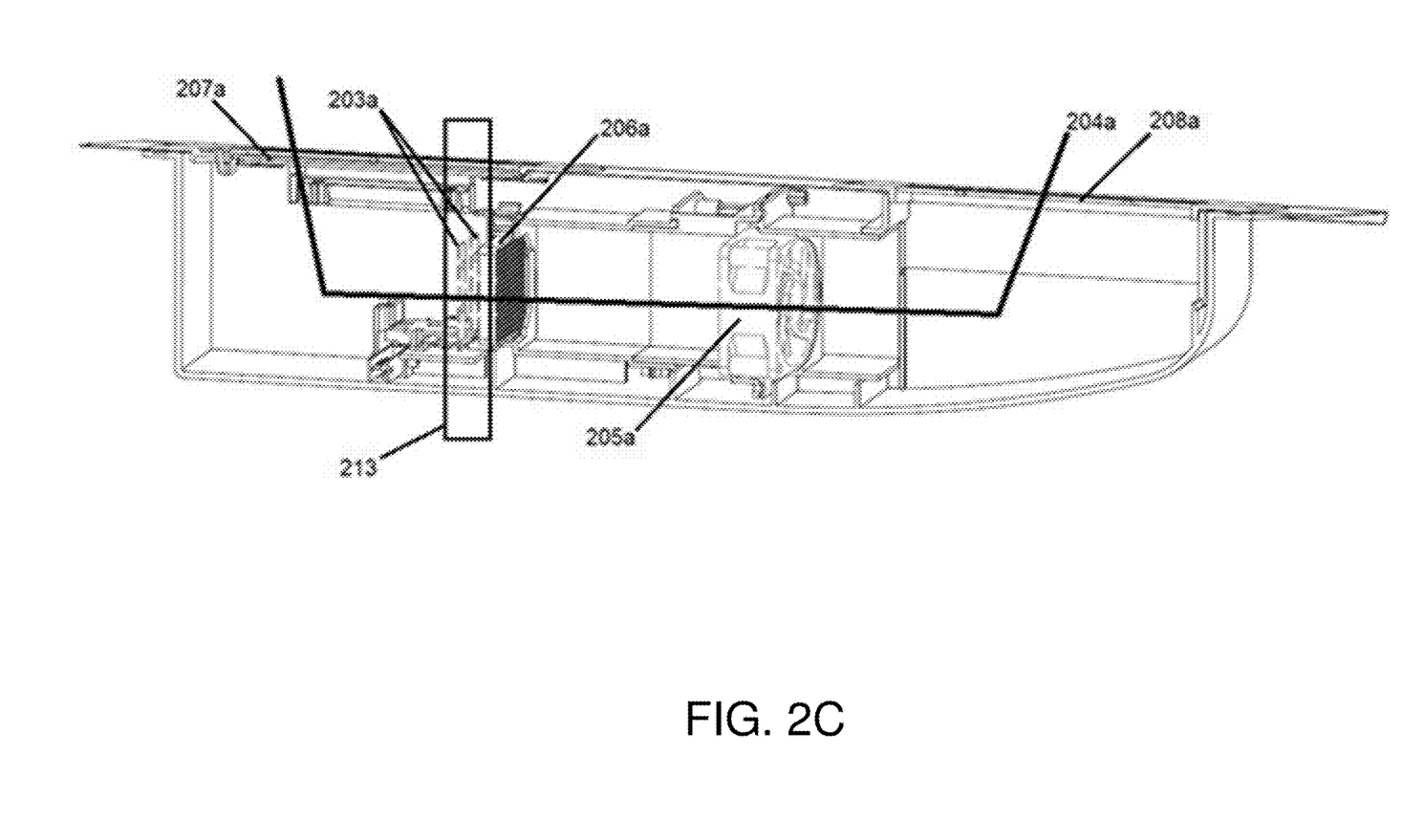
FIG. 2c schematically depicts a look-through view of one of the two airways of the troffer.

FIGS. 2a, 2b, and 2c show an embodiment of the lighting device of the present disclosure in a form of an LED troffer fixture 200. This troffer has a housing 201, the first light source 202a,202b, the second light source 203a,203b, two fans 205a,205b, two air filters 206a,206b, and two airways 204a,204b. The first light source comprises three rows of LEDs on three PCBs. Out of the three rows of LEDs, one row is 2700K LEDs 202a and the other two rows are 6500K LED 202b. The 2700K LEDs produce a lesser circadian stimulus and are more suitable for nighttime lighting, whereas the 6500K LED produce a higher circadian stimulus and are more suitable for daytime use. The combined light output of 2700K and 6500K LEDs sets the total light output of the lighting device. Since they each emits predominantly visible light in the >400 nm wavelength range, their combined light is also in the >400 nm wavelength range. A controller 212 is used to color-tune the light output of the light device by changing the mixing ratio of the light output of the 2700K LEDs 202a and the 6500K LEDs 202b. Though not shown, a memory module may be used to store a circadian schedule in the controller 212. The controller 212 can thus color-tune the light output of the first light source automatically according to the circadian schedule stored in the memory module. The circadian schedule will transition the color temperature of the first light source from warm white (2700K) to cold white (6500K) at dawn and revert the color temperature back to warm white at sunset, thus emulating color transition of the sunlight.

The construction of the two airways 204a and 204b are the same, therefore the description below is on the airway 204a. The second light source 203a in the airway 204a comprises multiple visible light LEDs and has little contribution to the light output of the lighting device. Because the second light source 203a is not completely conceal, its light may still leak out of the airway 204a, but it would never contribute more than 5% of the light output of the fixture. The airway 204a has an air inlet 207a and an air outlet 208a. The fan 205a and the air filter 206a are disposed inside the airway 204a. As the fan 205a forces the air through the airway 204a, the airborne microbials 210 are trapped on the surface of the air filter 206a.

Figure 2D:
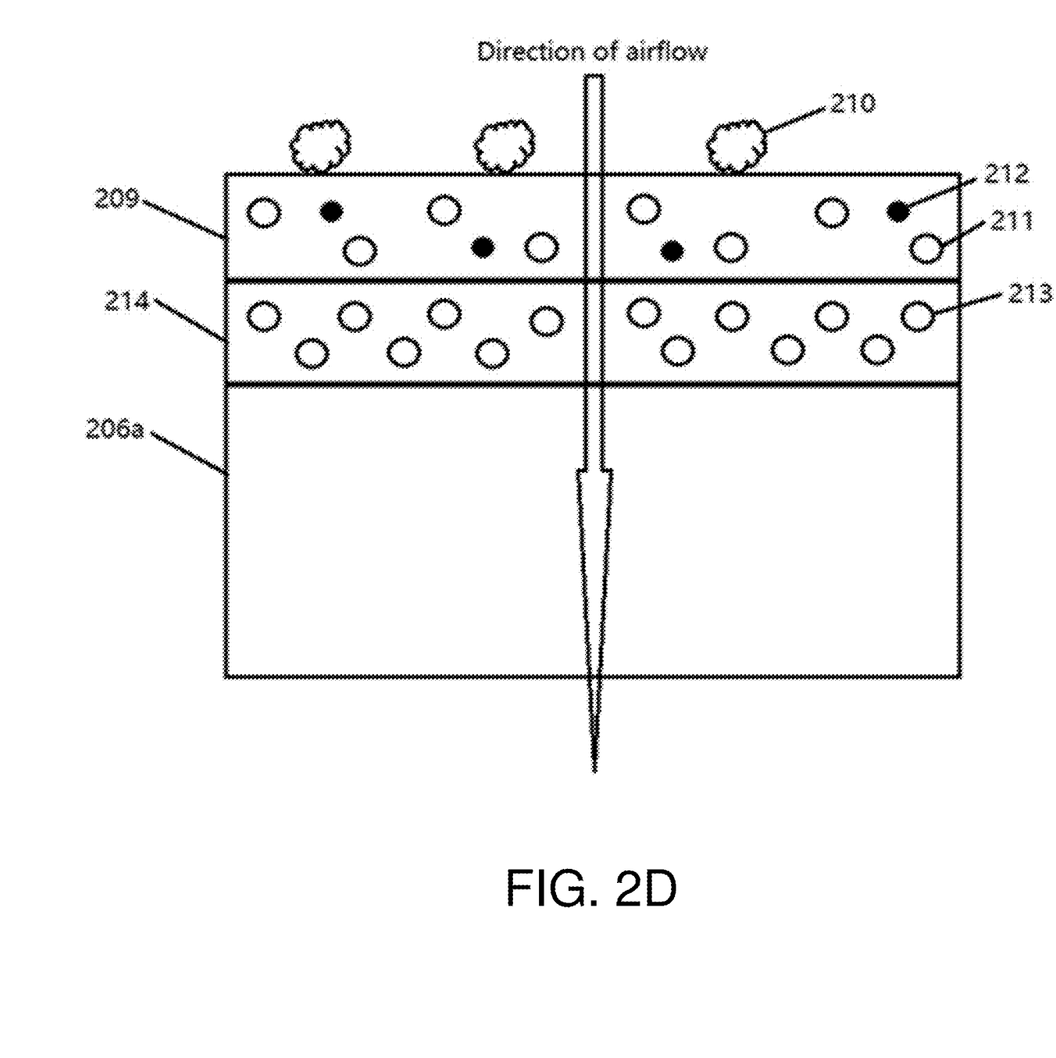
FIG. 2d schematically depicts the air filter and its activated carbon coating of the troffer, and the trapped microbials.

In FIG. 2d, as the air passes through the air filter 206a, the airborne microbials 210 are trapped on the surface of the air filter. The photocatalyst material in the antiviral photocatalytic coating 209 activated by the second light source 203a kills and decomposes the trapped microbials 210. The photocatalyst material contains nano anatase-type $TiO_2$ 211 as its primary photocatalyst and nano silver 212 as its secondary photocatalyst. The air filter 206a is further coated with an activated carbon 213 coating 214 for removing the gases and the bad odors in the air, as shown in FIG. 2d. Alternatively, a separate air filter containing activated carbon may be stacked together with the air filter 206a.

Figure 3:
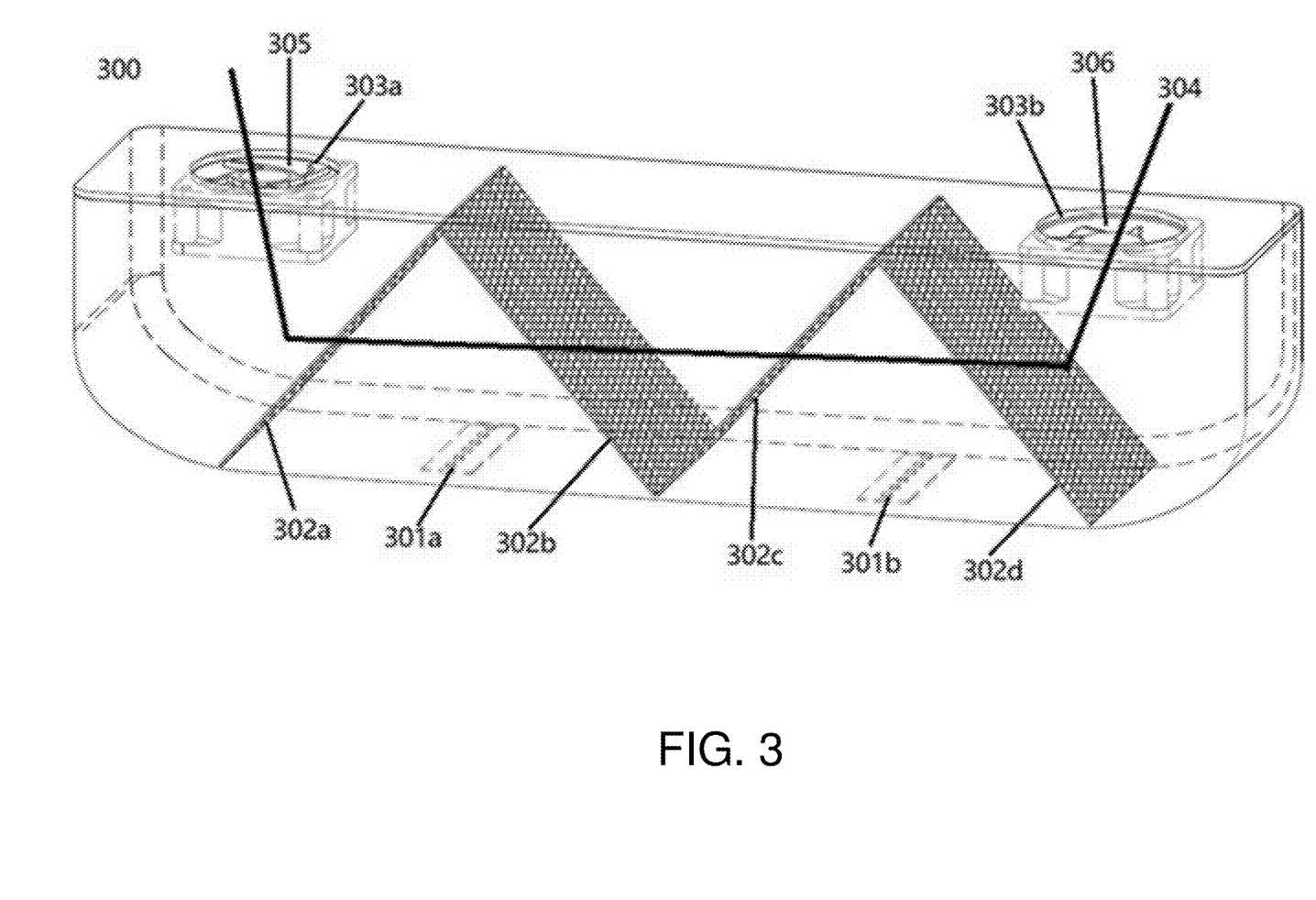
FIG. 3 schematically depicts a look-through view of another airway design of the LED troffer fixture using a multi-fold non-woven fabric air-filter.

FIG. 3 shows another design for the airway of the LED troffer. There are now four layers of air filter, 302a,302b, 302c,302d in the airway 304, and each air filter layer is made of non-woven fabric coated with a photocatalyst material (though not shown in the figure) containing nano anatase-type $TiO_2$ as its primary photocatalyst and nano silver as its secondary photocatalyst. The second light source 301a,301b comprises multiple visible light LEDs and has little contribution to the light output of the lighting device. Because the second light source 301a,301b is not completely concealed, its light may still leak out of the airway 304, but it would not contribute more than 5% of the light output of the fixture. The airway 304 has an air inlet 305 and an air outlet 306. The fan 303a pushes the ambient air into the airway 304, and the fan 303b pulls the air out of the airway 304 into the ambient environment. As the air is forced through the airway 304, the airborne microbials are trapped on the surface of the four air filter layers 302a,302b,302c,302d. The second light source 301a,301b activates the photocatalyst material on the four air filter layers 302a,302b,302c,302d, and the activated photocatalyst material kills and decomposes the microbials trapped on the air filters. The use of two fans for pushing-and-pulling of the air improves the airflow through the airway 304. The use of four layers of air filter 302a,302b, 302c,302d improves the air filtering effectiveness, and more importantly, the photocatalytic killing of the airborne microbials, since there are now four times the surface area with photocatalytic coating.

Figure 4:
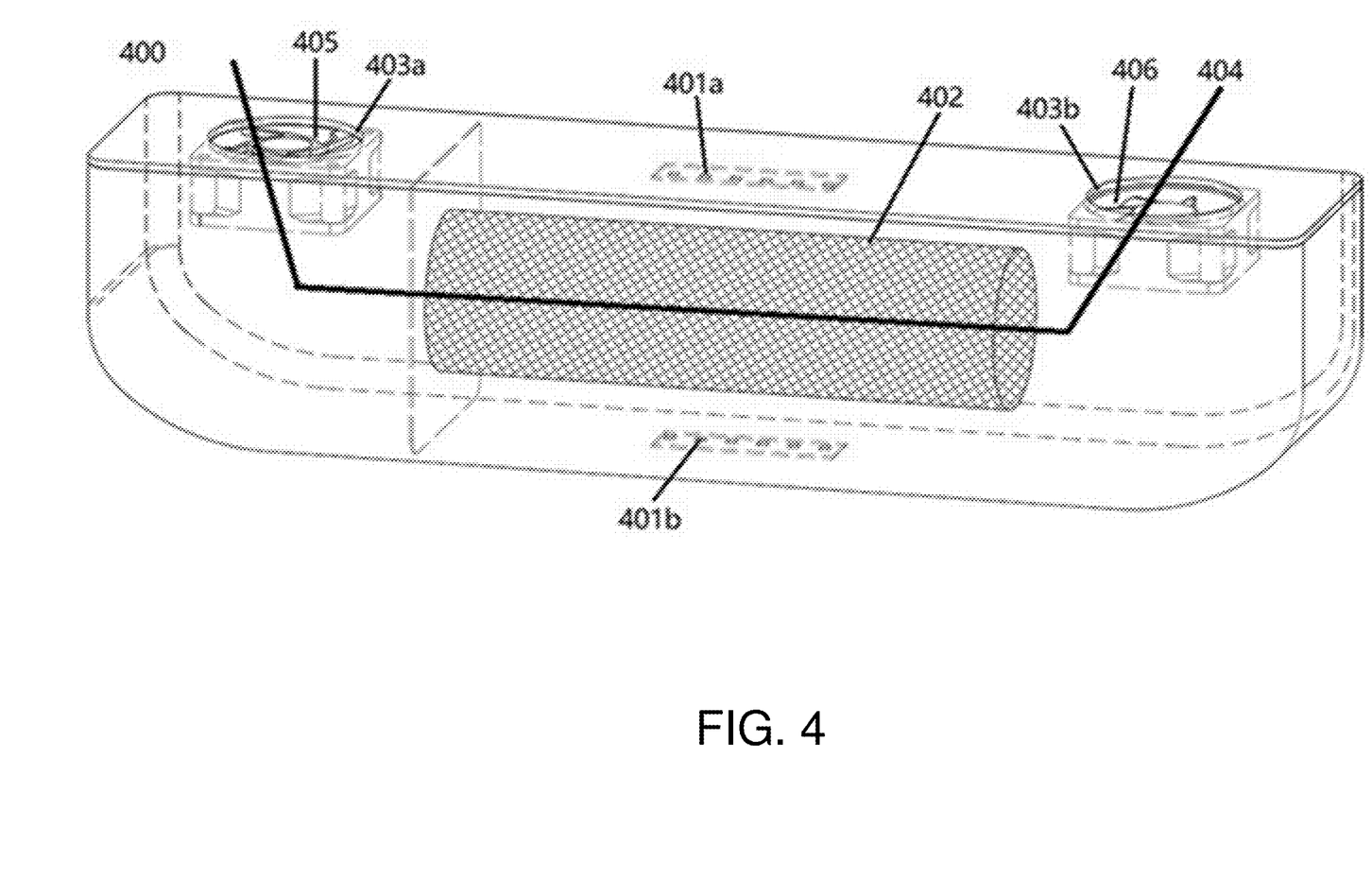
FIG. 4 schematically depicts a look-through view of another airway design of the LED troffer fixture using a cylindrical non-woven fabric air-filter.

FIG. 4 shows another design for the airway of the LED troffer 200. In this embodiment there is one cylindrical air filter 402 in the airway 404. The non-woven fabric air filter 402 is coated with a photocatalyst material (though not shown in the figure) containing nano anatase-type $TiO_2$ as its primary photocatalyst and nano silver as its secondary photocatalyst. The second light source 401a,401b comprises multiple visible light LEDs and has little contribution to the light output of the lighting device. Because the second light source 401a,401b is not completely concealed, its light may still leak out of the airway 404, but it would not contribute more than 5% of the light output of the fixture. The airway 404 has an air inlet 405 and an air outlet 406. The fan 403a pushes the ambient air into the airway 404, and the fan 403b pulls the air out of the airway 404 into the ambient environment. As the air is forced through the airway 404, the airborne microbials are trapped on the surface of the air filter 402. The second light source 401a,401b activates the photocatalyst material on the air filter 402, and the activated photocatalyst material kills and decomposes the microbials trapped on the air filter. The use of two fans for pushing-and-pulling of the air improves the airflow through the airway 404. The use of a cylindrical air filter improves the air filtering effectiveness, and more importantly, the photocatalytic killing of the airborne microbials, because of its large surface area with photocatalytic coating.

For an example of a fixture comprising only the air-disinfection module, simply remove from the LED troffer fixture 200 these components: the first light source 202a, 202b, and the controller 212.

Additional and Alternative Implementation Notes

Although the techniques have been described in language specific to certain applications, it is to be understood that the appended claims are not necessarily limited to the specific features or applications described herein. Rather, the specific features and examples are disclosed as non-limiting exemplary forms of implementing such techniques.

As used in this application, the term "or" is intended to mean an inclusive "or" rather than an exclusive "or." That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more," unless specified otherwise or clear from context to be directed to a singular form.

What is claimed is:

1. A lighting device, comprising:
    a housing;
    a first light source;
    a second light source;
    an air filter;
    an airway; and
    an air circulation mechanism corresponding to the airway,
    wherein, in operation:
        the housing houses the first light source, the second light source, the air filter, and the airway,
        the first light source emits a first visible light and accounts for at least 90% of a light output of the lighting device,
        the second light source emits a second visible light and accounts for less than 10% of the light output of the lighting device,
        the second light source is disposed inside the airway,
        the airway has an air inlet and an air outlet,
        the air circulation mechanism sucks an ambient air through the air inlet, forces the air through the air filter, and releases the air through the air outlet,
        the air filter traps airborne particles carried in the air,
        the air filter has an antiviral photocatalytic coating on a surface thereof,
        the second light source is disposed adjacent to the air filter and activates a visible-light photocatalyst material in the antiviral photocatalytic coating, and
        airborne microbials trapped by the air filter are decomposed by the activated photocatalyst material in the antiviral photocatalytic coating.

2. A lighting device of claim 1, wherein the second light source emits no ultraviolet wavelength.

3. A lighting device of claim 1, wherein the visible-light activatable photocatalyst material in the antiviral photocatalytic coating on the air filter contains titanium oxide ($TiO_2$).

4. A lighting device of claim 1, wherein the visible-light activatable photocatalyst material in the antiviral photocatalytic coating on the air filter contains titanium oxide ($TiO_2$) as a primary photocatalyst and an active metal ingredient as a secondary photocatalyst, and wherein the active metal ingredient comprises silver, gold, copper, zinc, nickel, or a combination thereof.

5. A lighting device of claim 1, wherein the visible-light activatable photocatalyst material in the antiviral photocatalytic coating on the air filter contains a noble metal nanoparticle gold (Au) or sliver (Ag) as a main photocatalyst.

6. A lighting device of claim 1, wherein the air filter comprises multiple layers or folds.

7. A lighting device of claim 1, wherein the air filter is of a cylindrical shape.

8. A lighting device of claim 1, wherein the air filter contains a non-woven fabric.

9. A lighting device of claim 1, wherein the air filter contains an activated carbon.

10. A lighting device of claim 1, wherein the air circulation mechanism comprises at least one fan disposed in the airway.

11. A lighting device of claim 10, wherein the at least one fan comprises a first fan and a second fan, and wherein the first fan sucks the ambient air into the airway and the second fan pulls the air out of the airway.

12. A lighting device of claim 1, wherein the first light source comprises emitting diodes (LEDs).

13. A lighting device of claim 1, wherein the second light source comprises light emitting diodes (LEDs).

14. A lighting device of claim 1, wherein the first light source further comprises a third light source and a fourth light source, wherein the third light source and the fourth light source together emit the first visible light, and wherein a color temperature of the third light source is higher than a color temperature of the fourth light source.

15. A lighting device of claim 14, further comprising:
a controller,
wherein the controller is configured to tune a color temperature of the first light source by mixing a combination ratio of the color temperatures of the third light source and the fourth light source, either manually or automatically, according to a circadian schedule stored in a memory module of the controller.

16. A lighting device, comprising:
a housing;
a light source;
an air filter;
an airway; and
an air circulation mechanism corresponding to the airway, wherein, in operation:
the housing houses the light source, the air filter, and the airway,
the light source emits a visible light,
the light source is disposed inside the airway,
the airway has an air inlet and an air outlet,
the air circulation mechanism sucks an ambient air through the air inlet, forces the air through the air filter, and releases the air through the air outlet,
the air filter traps airborne particles carried in the air,
the air filter has an antiviral photocatalytic coating on a surface thereof,
the light source is disposed adjacent to the air filter and activates a visible-light photocatalyst material in the antiviral photocatalytic coating, and
airborne microbials trapped by the air filter are decomposed by the activated photocatalyst material in the antiviral photocatalytic coating.

17. A lighting device of claim 16, wherein the light source emits no ultraviolet wavelength.

18. A lighting device of claim 16, wherein the visible-light activatable photocatalyst material in the antiviral photocatalytic coating on the air filter contains titanium oxide ($TiO_2$).

19. A lighting device of claim 16, wherein the visible-light activatable photocatalyst material in the antiviral photocatalytic coating on the air filter contains titanium oxide ($TiO_2$) as a primary photocatalyst and an active metal ingredient as a secondary photocatalyst, and wherein the active metal ingredient comprises silver, gold, copper, zinc, nickel, or a combination thereof.

20. A lighting device of claim 16, wherein the air filter contains a non-woven fabric.

21. A lighting device of claim 16, wherein the air circulation mechanism comprises at least one fan disposed in the airway.

22. A lighting device of claim 16, wherein the light source comprises emitting diodes (LEDs).

* * * * *